(12) United States Patent
Moorcroft et al.

(10) Patent No.: US 6,328,737 B1
(45) Date of Patent: Dec. 11, 2001

(54) FRACTURE REDUCTION DEVICE

(75) Inventors: Ian Moorcroft, Stone; Peter Ogrodnik, Weston; Peter Thomas, Crewe, all of (GB)

(73) Assignees: Keel University; Strafforshire University Enterprises Limited, both of Straffordshire (GB)

( * ) Notice: Subject to any disclaimer, the term of this patent is extended or adjusted under 35 U.S.C. 154(b) by 0 days.

(21) Appl. No.: 09/402,844

(22) PCT Filed: Apr. 14, 1998

(86) PCT No.: PCT/GB98/00884

§ 371 Date: Mar. 3, 2000

§ 102(e) Date: Mar. 3, 2000

(87) PCT Pub. No.: WO98/46156

PCT Pub. Date: Oct. 22, 1998

(30) Foreign Application Priority Data

Apr. 11, 1997 (GB) .................................................. 9707421

(51) Int. Cl.[7] .................................................. A61B 17/60
(52) U.S. Cl. .................................................. 606/57
(58) Field of Search .................................. 606/57, 58, 59, 606/54

(56) References Cited

U.S. PATENT DOCUMENTS

| | | | |
|---|---|---|---|
| 2,020,262 | * 11/1935 | Longfellow | 606/54 |
| 2,035,952 | * 3/1936 | Ettinger | 606/59 |
| 2,238,870 | * 4/1941 | Haynes | 606/59 |
| 2,371,519 | * 3/1945 | Haynes | 606/59 |
| 2,406,987 | * 9/1946 | Anderson | 606/59 |
| 4,365,624 | * 12/1982 | Jaquet | 606/57 |
| 4,889,111 | * 12/1989 | Ben-Dov | 606/59 |
| 4,988,349 | 1/1991 | Pennig . | |
| 5,152,280 | 10/1992 | Danieli . | |
| 5,437,666 | 8/1995 | Tepic et al. . | |
| 5,454,810 | 10/1995 | Pohl . | |

FOREIGN PATENT DOCUMENTS

| | | |
|---|---|---|
| 0490812A1 | 6/1992 | (EP) . |
| 0784962A | 7/1997 | (EP) . |
| 2001533A | 2/1979 | (GB) . |
| 2164859A | 3/1986 | (GB) . |
| WO9202184A | 2/1992 | (WO) . |
| WO9619944A | 4/1996 | (WO) . |
| WO9820802A | 5/1998 | (WO) . |

* cited by examiner

Primary Examiner—Eduardo C. Robert
(74) Attorney, Agent, or Firm—Woodard, Emhardt, Naughton, Moriarty & McNett

(57) ABSTRACT

A fracture reduction device comprises linear adjustment means for linearly reducing a fractured bone in three directions, and angular adjustment mechanism for angularly reducing a fractured bone about three independent axes. The adjustment mechanism is such that adjustment in each direction and about each axis is independent of the others. The device also allows stable incremental adjustments to be made to the bone position and/or orientation.

12 Claims, 5 Drawing Sheets

FRACTURE REDUCTION DEVICE

FIELD OF THE INVENTION

The present invention relates to fracture reduction devices.

BACKGROUND OF THE INVENTION

A variety of techniques are known for holding together the parts of a fractured bone while healing takes place. One such technique is external fixation, in which pins are inserted into the bone on each side of the fracture point, and which are then connected to a frame by adjustable clamps. The clamps can then be tightened to hold the parts of the bone fixed with respect to each other.

However, before such fixation can take place, the fracture must be reduced so that the bone fragments are in the correct positions for fixation and healing.

Previously considered reduction devices allow such reduction to be controlled, but are inconvenient since it is not simple to control a single degree of freedom of movement independently of the other degrees of freedom.

It is desirable to provide a fracture reduction apparatus in which controlled vector separation can be easily and simply achieved.

SUMMARY OF THE INVENTION

According to the present invention there is provided a fracture reduction device comprising linear adjustment means and angular adjustment means for reducing a fractured bone, the adjustment means allowing stable incremental adjustments to be made to the bone position and/or orientation, the adjustment means comprising:

a substantially rigid support structure;

first and second loading supports attached to the support structure for attachment to first and second portions of a fractured limb about a fracture site, the loading supports being arranged such that the limb can be subjected to a longitudinal distractive force by means of the loading supports; and first and second bone supports for supporting first and second portions of a fractured bone about the fracture site;

one of the first and second loading supports being rotatable with respect to the other loading support about two mutually perpendicular axes;

at least one of the first and second bone supports being movable in two linear directions perpendicular to one another and to the longitudinal direction of the bone; and wherein adjustment of the positions of the loading and bone supports allows stable incremental adjustments to be made to the bone position and/or orientation.

The provision of adjustment means which allow incremental adjustment to be made enables a fractured bone to undergo gradual vector separation in order to improve the healing process. Such incremental adjusters are preferably screw-threaded, but could be provided by some suitable alternative.

Once reduction is complete, a bone fixator may be fitted and the reduction device removed.

BRIEF DESCRIPTION OF THE DRAWINGS

For a better understanding of the invention, and to show how the same may be carried into effect, reference will now be made, by way of example, to the accompanying drawings, in which.

DESCRIPTION OF THE PREFERRED EMBODIMENTS

Figure 1:
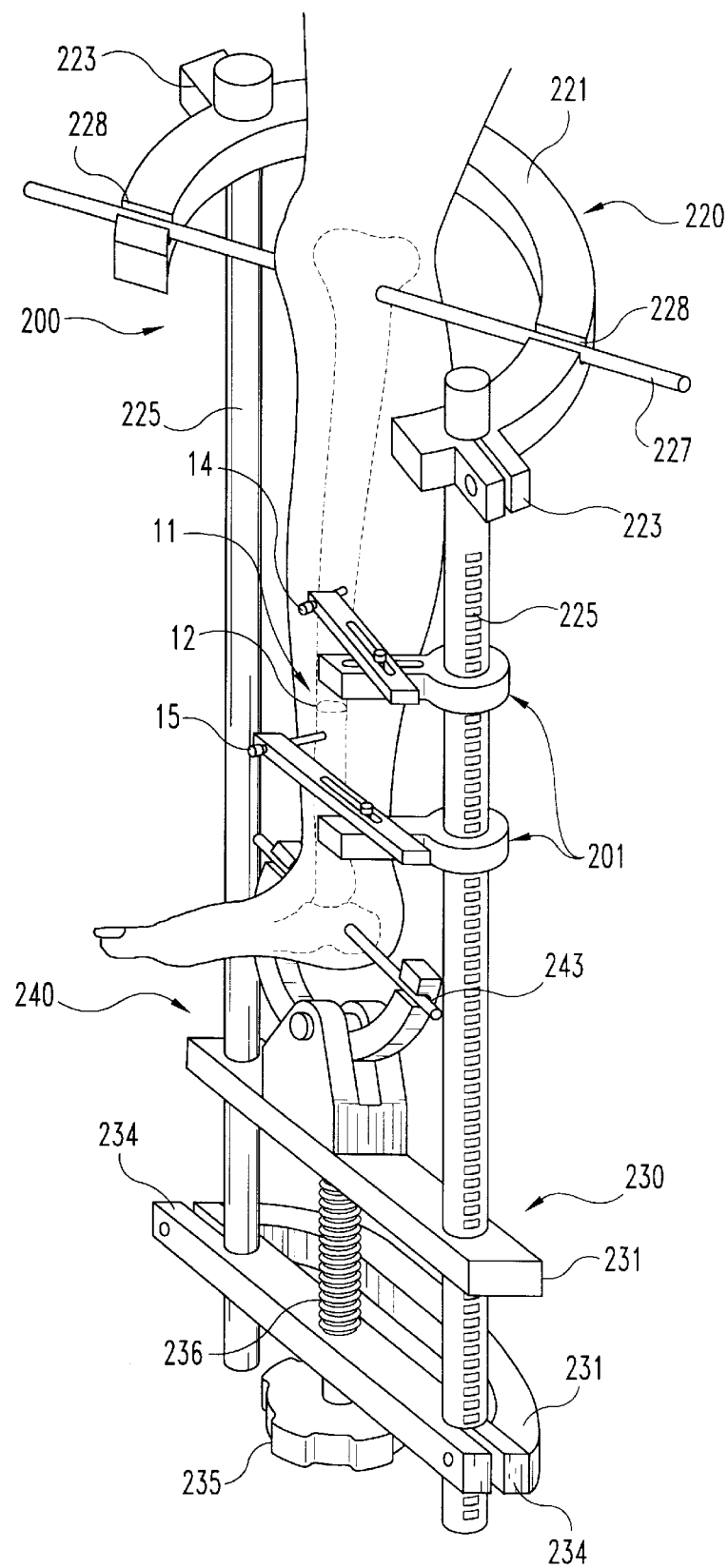
FIG. 1 shows a schematic view of an embodiment of the present invention, applied to a fractured leg.

FIG. 1 shows a schematic diagram of an embodiment of the present invention applied to a fractured leg bone 1 having a fracture site 11 and proximal and distal bone fragments 10 and 12. The device 200 is attached to a patient using two rods 227 and 243. The first (proximal) rod 227 passes through the leg at or about the knee and the second (distal) 243 passes through the leg at or around the ankle. These rods allow a tensile force to be applied to the broken bone 10.

Two bone pins 14 and 15 are attached close to the fracture site 11, the bone pins are generally uni-cortical, and the reduction device 200 is attached to the bone pins. The use of uni-cortical bone pins, which may be inserted using normal clinical methods, allows later use of conventional intra-medullary nailing.

An initial distractive (longitudinal) force can be applied directly using the device 200 of FIG. 1. The reduction process can then take place before the bone is fixed using a fixation device.

The device 200 comprises two support tubes 225 which extend parallel to the leg bone 1 and which extend from a proximal end fixing arrangement 220 to a distal end fixing arrangement 230. The proximal end fixing arrangement 220 comprises a substantially C-shaped bracket 221 having clamp regions 223 to which the support tubes 225 are rigidly attached. The proximal end rod 227 is held in slots 228 in the bracket 221. The side support tubes extend to a distal end bracket 223 and are rigidly clamped thereto by clamps 234.

A mounting plate 231 is slidably mounted on the tubes 225 and carries a distal end attachment 240, which will be described in more detail below. The attachment 240 holds the distal end support rod 243 which passes through the distal end of the bone.

Figure 2:
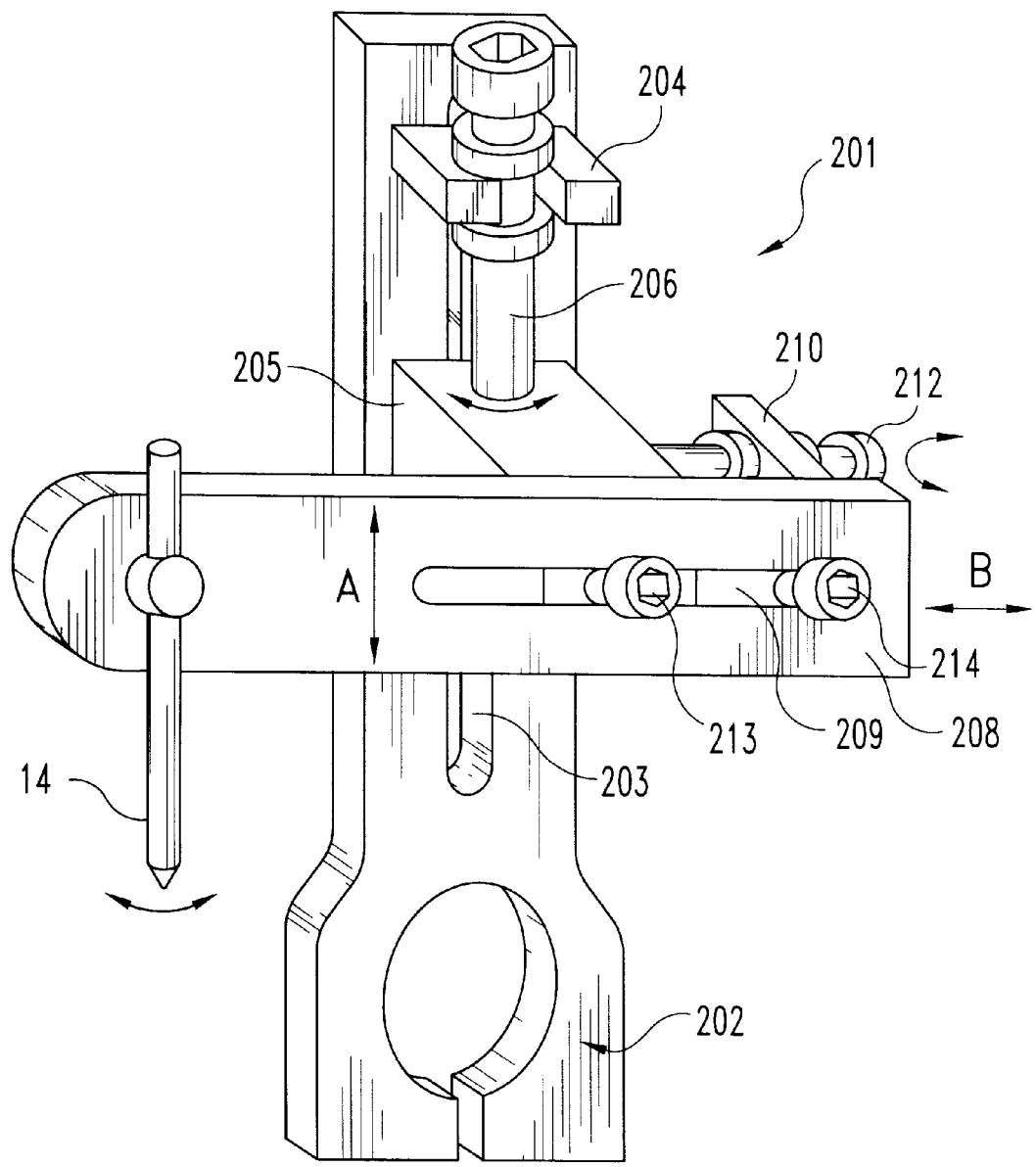
FIG. 2 shows an enlarged view of part of the embodiment of FIG. 1.

Bone pin brackets 201 are slidably engaged on one of the support tubes 225 as shown in FIG. 1, and will now be described with reference to FIG. 2.

Each bone pin bracket 201 is adjusted for longitudinal position and then clamped to the side tube 225. Bone pins 14 and 15 are inserted into respective bone fragments 10 and 12 and have their position, and hence the fracture position, controlled by the device 200 via the brackets 201. Each bracket includes a main bracket body 202 which clamps to the side tube when in use, and which defines a slot 203. An adjustment block 205 is arranged to engage with the slot 203 and thereby be slidable along the main body 202. A flange 204 extends from the body 202 and supports an adjustment screw 206. The adjustment screw 206 engages with the block 205 so that the position of the block can be controlled and adjusted as required by turning of the screw 206.

A plate 208, which defines a slot 209, is carried on the block 205 by means of a fixing screw 213. A flange 210 extends from the plate 208 and is secured thereto by a screw 214. The flange 210 supports a second adjustment screw 212, which engages with the block 205. The plate 208 carries the bone pin 14, 15.

Adjustment of the bone pin position is achieved by rotating the adjustment screws 206 and 212. Rotating screw 206 moves the pin in a vertical direction shown by arrow A (up/down) which is the sagittal direction, and rotating the adjustment screw, 212 moves the pin in a lateral direction shown by arrow B (the coronal translation).

The bone pin brackets allow the two directions of adjustment to be adjusted independently of one another and without causing unwanted uncontrolled movement at the fracture site 11.

Figure 3:
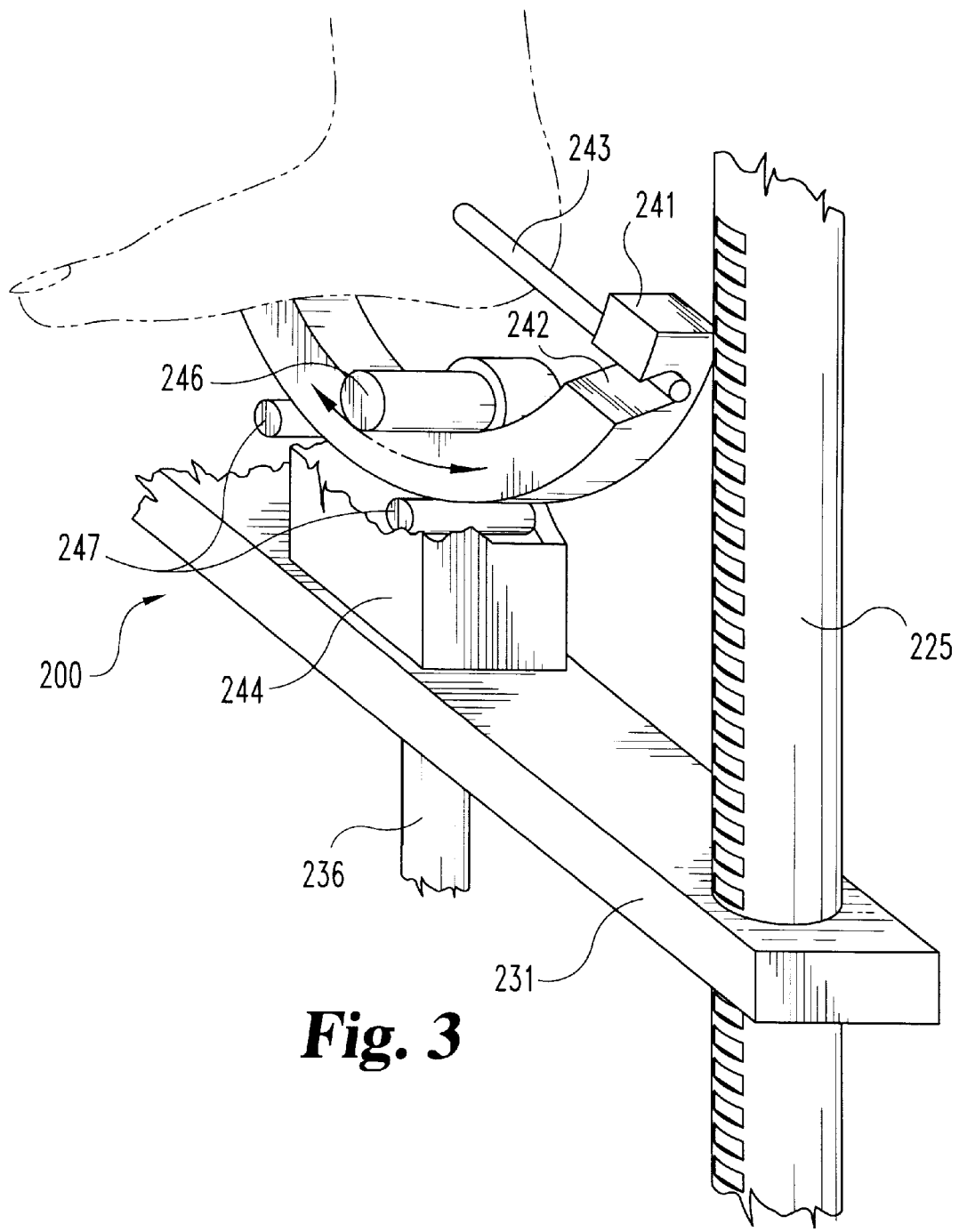
FIG. 3 shows an enlarged view of another part of the FIG. 1 embodiment.

FIG. 3 shows an enlarged view of the second end fixing system 240. A mounting plate 231 is slidably engaged with the side support tube 225 and carries a support block 244. In turn, the support block 244 carries three rollers 246 and 247. A substantially C-shaped bracket 241 is slidably engaged with these rollers. The bracket 241 carries the distal fixing rod 243 in slots 242. The rod 243 passes through a distal part of the leg.

Sliding the C-shaped bracket 241 through the rollers 246 and 247, enables the angular displacement of the leg to be adjusted in the coronal plane (i.e. about an axis perpendicular to the longitudinal and lateral/coronal directions). The movement of the bracket 241 can be controlled by frictional engagement with the rollers 246 and 247, or by a fixing screw (not shown).

Figure 4:
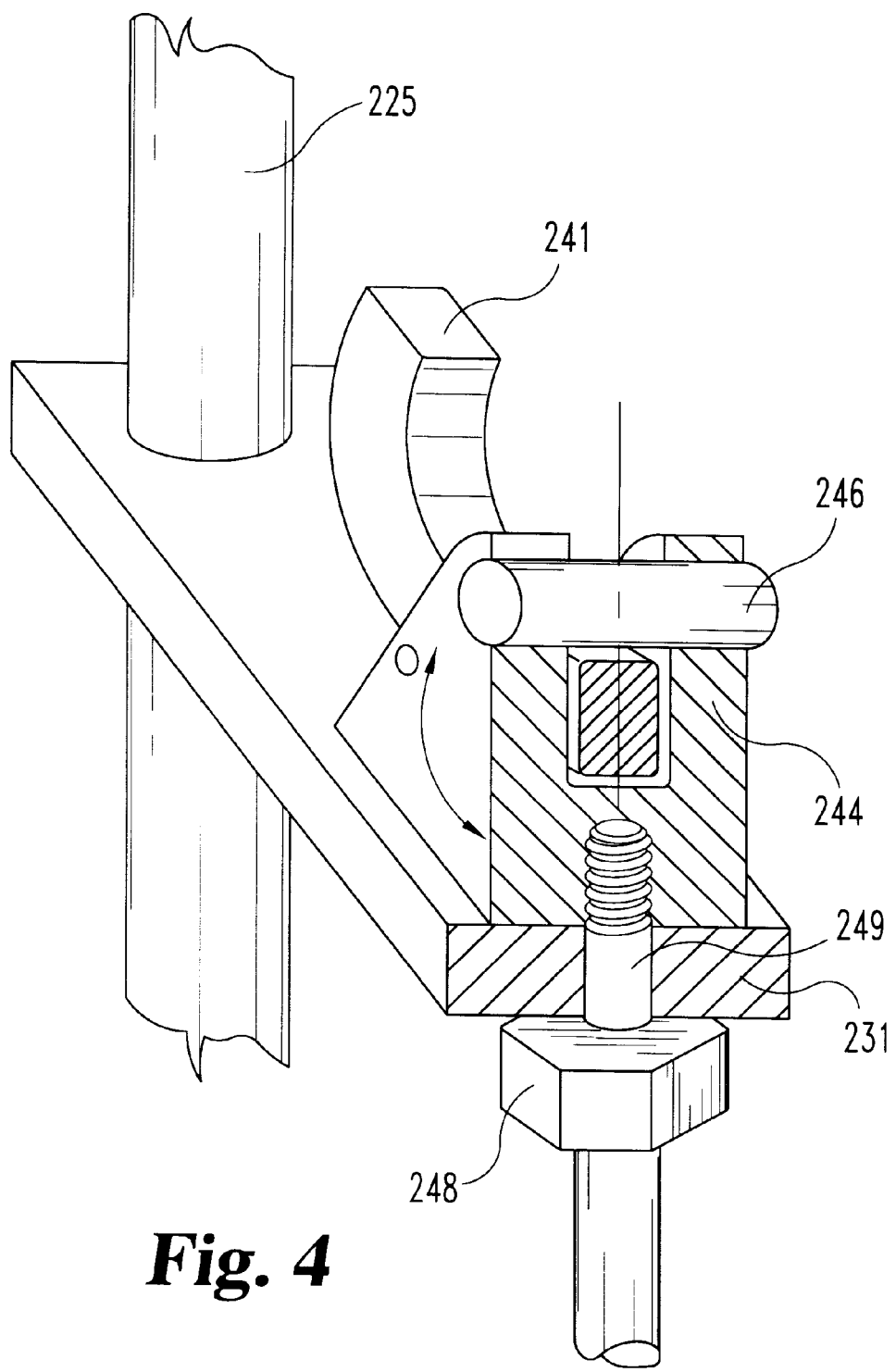
FIG. 4 shows an enlarged view of yet another part of the FIG. 1 embodiment.

FIG. 4 shows a cross-sectional view of further details of the distal fixing arrangement 240. The support block 244 is held on the mounting plate 231 by means of a nut 248 and bolt 249 arrangement. When the nut 248 is slackened, the support block 244 is able to rotate about the longitudinal axis of the device, thereby enabling the angular position of the leg, and the distal bone fragment 12 to be adjusted with respect to the proximal bone fragment 10. When the required angular displacement is achieved, the nut 248 can be locked thereby fixing the relative positions.

Figure 5:
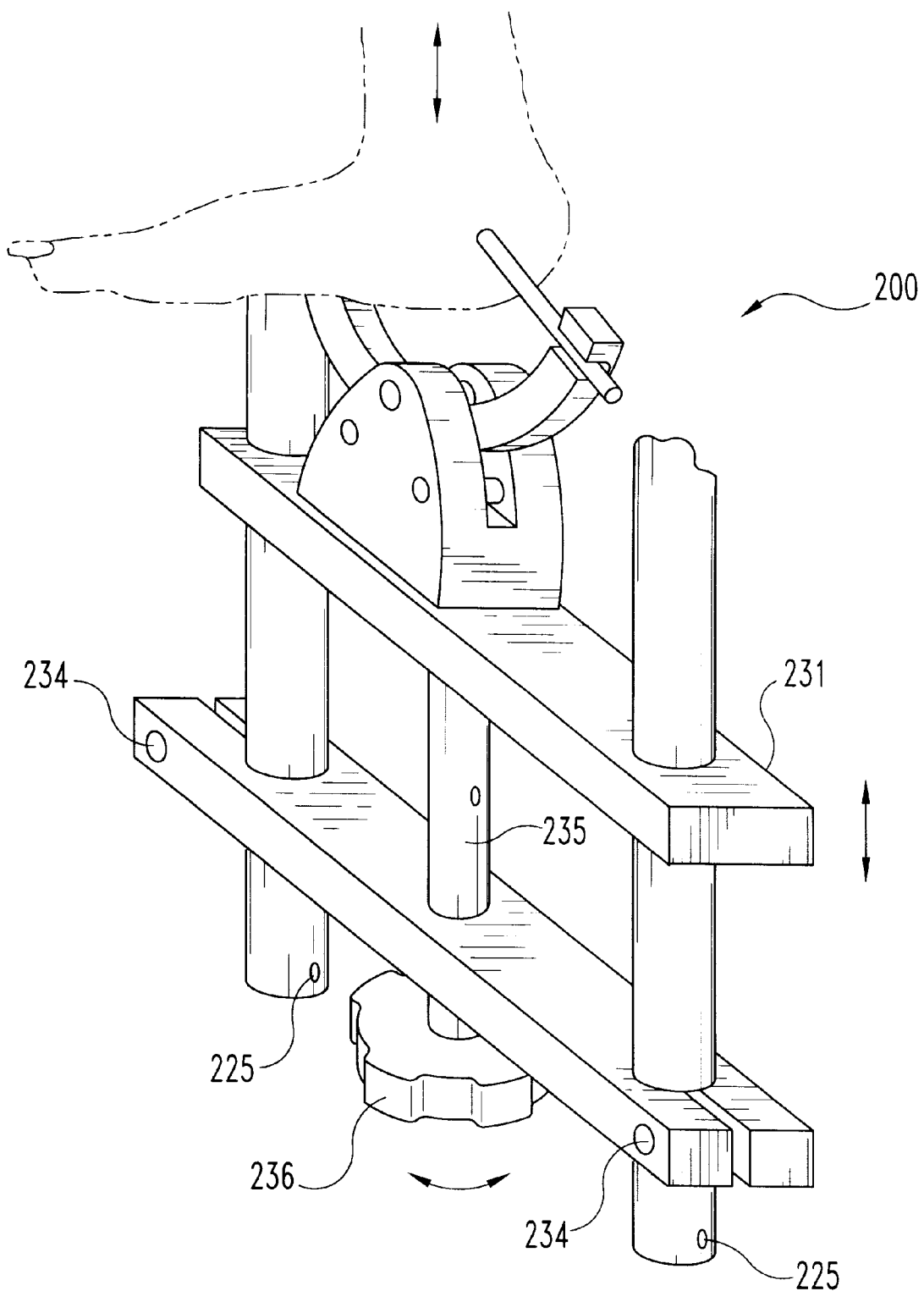
FIG. 5 shows an enlarged view of a further part of a FIG. 1 embodiment.

FIG. 5 shows a view of the further details of the fixing arrangement 240. A support plate 233 is rigidly attached to the support bars 225 by means of clamps 234. This provides a rigid reference point for longitudinal movement of the device. A threaded adjustment screw 235 extends from the sliding support plate and is in threaded engagement with the fixed support plate 234. A handle 236 is rigidly attached to the free end of the adjustment screw 235, so that rotation of the handle causes the screw 235 to rotate, thereby adjusting the position of the sliding support plate 231 by virtue of the threaded engagement between the screw and the rigid support plate.

The arrangement shown in FIG. 5 allows longitudinal extension (traction) to be applied to the leg by simply turning the screw 235. Such adjustment is independent of the other position adjustments.

It will be appreciated that a device embodying the present invention allows adjustment to be made to the bone fragment positions in each of six degrees of freedom.

Furthermore, the embodiment described allows stable incremental adjustments (vector separation) to be made during the reduction process. In contrast, previously-considered reduction devices have required almost complete slackening of adjustment bolts etc. to enable adjustments to be made.

The described embodiment of the invention includes adjustment mechanisms which hold their position, even when undergoing adjustment.

One advantage of this design is that repeated separation/reduction of the fractured bone can be easily achieved. Simply turning the screw threaded adjusters enables such incremental adjustment.

Other major advantages of the above described device embodying the present invention are:
   Repeatably better anatomical reduction, through the provision of independent adjusters;
   Repeatably better operating times, up to 50% less than with conventional devices, achieved by virtue of the simple design;
   Minimal interference at the fracture site. This enables easy access for X-ray or image intensifier equipment, for judging the reduction process, and for easier access for attaching a fixator; and
   Since there are no bi-cortical pins used in the preferred embodiments, the device is suitable for use with intra-medullary nailing.

What is claimed is:

1. A fracture reduction device comprising adjustment means for reducing a fractured bone, the adjustment means allowing stable incremental adjustments to be made to the bone position and orientation, the adjustment means comprising:
   a substantially rigid support structure;
   first and second loading supports attached to the support structure for attachment to first and second portions of a fractured limb about a fracture site, the loading supports being arranged such that the limb can be subjected to a longitudinal distractive force by means of the loading supports; and
   first and second bone supports for supporting first and second portions of a fractured bone about the fracture site;
   one of the first and second loading supports being rotatable with respect to the other loading support about two mutually perpendicular axes;
      wherein the bone defines a longitudinal direction and wherein at least one of the first and second bone supports is movable in two linear directions perpendicular to one another and to the longitudinal direction of the bone; and
      wherein adjustment of the positions of the loading and bone supports allows stable incremental adjustments to be made to the bone position and orientation.

2. A fracture reduction device according to claim 1, wherein both of the first and second bone supports are movable in two linear directions perpendicular to one another and to the longitudinal direction of the bone.

3. A fracture reduction device according to claim 1, wherein the first and second bone supports are capable of supporting the first and second portions of the bone at locations immediately adjacent the fracture site.

4. A fracture reduction device according to claim 1, wherein the first and second bone supports are attachable to the limb by strapping or the like, or are attachable directly to the bone portions by bone pins or the like.

5. A fracture reduction device according to claim 1, wherein said rigid support comprises at least one elongate member capable of extending across the fracture site.

6. A fracture reduction device according to claim 5, wherein the support structure comprises two said elongate members positionable on opposing sides of the limb, the first and second loading supports being secured between said two elongate members.

7. A fracture reduction device according to claim 1, wherein said rotatable one of the first an second loading supports is said first loading support, and wherein said at least one movable one of the first and second bone supports said first bone support.

8. A fracture reduction device according to claim 1, wherein said rotatable loading support comprise a substantially C shaped member having two arms locatable on opposite sides of the limb, the loading support being attachable to the limb by way of an elongate member extending between said two arms and through the limb, the C shape member being supported between rollers which allow the C shaped member to rock back and forth enabling rotation of the limb about one of said axis.

9. A fracture reduction device according to claim 8, wherein the C shaped member and rollers are supported by a support member mounted other support structure so as to be rotatable about said longitudinal direction.

10. A fracture reduction device according to claim 1, wherein one of said loading supports is slidably mounted upon said support structure and means are provided for controllably moving the loading support along said longitudinal axis towards and away from the other loading support to produce said longitudinal force.

11. If A fracture reduction device according to claims 10, wherein the movable loading support is the first loading support.

12. If A fracture reduction device according to claim 1, wherein the incremental adjusters are screw-threaded.

\* \* \* \* \*

UNITED STATES PATENT AND TRADEMARK OFFICE
CERTIFICATE OF CORRECTION

PATENT NO. : 6,328,737 B1 Page 1 of 1
DATED : December 11, 2001
INVENTOR(S) : Moorcroft et al.

It is certified that error appears in the above-identified patent and that said Letters Patent is hereby corrected as shown below:

<u>Title page,</u>
Item [75], Inventors, please delete the word "Stone" and add -- Staffordshire --.
Item [75], Inventors, please delete the word "Weston" and add -- Staffordshire --.
Item [75], Inventors, please delete the word "Crewe" and add -- Cheshire --.
Item [73], Assignees, please delete the word "Keel" and add -- Keele --
Item [73], Assignees, please delete the word "Strafforshire" and add -- Staffordshire --.
Item [73], Assignees, please delete the word "Straffordshire" and add -- Staffordshire --.

<u>Column 6,</u>
Line 8, please delete the word "If"
Line 11, please delete the word "If"

Signed and Sealed this

Sixth Day of August, 2002

*Attest:*

*Attesting Officer*

JAMES E. ROGAN
*Director of the United States Patent and Trademark Office*